United States Patent [19]

Ogasa

[11] 4,147,773

[45] Apr. 3, 1979

[54] POWDERY COMPOSITION COMPRISING VIABLE BIFIDOBACTERIA CELLS AND LACTULOSE

[75] Inventor: Katsuhiro Ogasa, Yokohama, Japan

[73] Assignee: Morinaga Milk Industry Co., Ltd., Tokyo, Japan

[21] Appl. No.: 859,713

[22] Filed: Dec. 12, 1977

[51] Int. Cl.$^2$ ............................................ A61K 37/00
[52] U.S. Cl. ........................................................ 424/93
[58] Field of Search ........................................... 424/93

[56] References Cited

U.S. PATENT DOCUMENTS 3,072,528  1/1963  Kludas et al. ........................... 424/93

*Primary Examiner*—Sam Rosen
*Attorney, Agent, or Firm*—Oblon, Fisher, Spivak, McClelland & Maier

[57] ABSTRACT

An orally administered powdery composition comprising freeze dried viable cell mass of the genus Bifidobacterium and powdered lactulose is effective for the establishment of favorable Bifidobacteria in cases of abnormal intestinal flora.

The composition contains viable cell mass of the genus Bifidobacterium, has a high cell density not less than $8 \times 10^{10}$ per gram, and exhibits a high cell survival rate over a long period of storage.

5 Claims, No Drawings

POWDERY COMPOSITION COMPRISING VIABLE BIFIDOBACTERIA CELLS AND LACTULOSE

BACKGROUND OF THE INVENTION

This invention generally relates to a powdery composition comprising dried viable cell mass of the genus Bifidobacterium (hereinafter described as Bifidobacteria cells) to be orally administered for initiation or conservation of favorable intestinal flora.

More particularly this invention relates to a powdery composition comprising a powder containing viable Bifidobacteria cells and lactulose which composition has a high survival rate for a long period of storage.

It has been well known that Bifidobacterium is normally found in the human intestine, and is one of the useful microorganisms.

Also it has been known that oral administration of viable Bifidobacteria cells is effective for preventing and treating bowel complaints, particularly diarrhea, intestinal catarrh, dyspepsia, constipation and intestinal microbial substitution (microbisme substitué) after treatment with antibiotics. For such purposes, a variety of powdery compositions containing dried viable Bifidobacteria cells have been sold in the market.

In the conventional powdery compositions, however, the survival rate of Bifidobacteria cells has been unsatisfactorily low, and it has been a basic problem to improve the cell survival rate and preserve the viable count of Bifidobacteria cells at a certain level for a long period of storage.

For instance, the content of viable Bifidobacteria cells in 1 gram of the powdery products supplied by the 12 companies in Japan and of the powdered milk containing Bifidobacteria cells and a small portion of lactulose supplied by a certain German company is generally as low as 5 or $6 \times 10^7$ or so. Moreover, the viable count of the cells in these products rapidly decreases during storage.

Under such circumstances, many attempts at improving the shelf life of products containing Bifidobacteria cells have been made.

Ohta reported in his research note entitled "Research for freezing and freeze drying Lactobacillus bifidus" in the Japanese journal "Ochanomizu Igaku Zasshi (Ochanomizu Medical Journal)" Vol. 7, No. 11 (1959), pp. 2967-2975, concerning the viability of freeze dried Bifidobacteria cells which were prepared with various drying methods and suspending agents.

In this research note, he reported that sodium glutamate as a suspending medium for freeze drying of Bifidobacteria cells may give a better cell survival rate when freeze dried Bifidobacteria cells were stored at 37° C., and skim milk, soluble starch and sucrose followed thereafter. The best results were observed when sodium glutamate in 3% (by weight) concentration was used, but the survival rate in this best case decreased to 1% after only 2 months storage.

Smiha reported in the "Journal of Food Science" Vol. 39 (1974) pp. 641-642 that a 55% survival rate after 2 months storage at 30° C. was obtained when Lactobacillus bifidus (old scientific nomenclature for genus Bifidobacterium) cells were subjected to freeze drying using a suspending agent of skim milk fortified with ascorbic acid, thiourea and ammonium chloride. This value is somewhat higher but the product prepared by this method is not preferable for the usual distributing system, since the viable count of Lactobacillus bifidus in this product is considered to rapidly decrease upon prolonged storage, i.e., more than 2 months.

As mentioned above, decreased survival rate during storage greatly impairs the commercial value of such powdery products, since the density of Bifidobacteria cells decreases during storage even if the products initially have a high cell density.

Consequently, in the conventional products containing viable Bifidobacteria cells, lactose, starch and the like have been added as a suspending medium for protection of the cells. Nevertheless, the conventional powdery compositions containing a known suspending medium do not achieve sufficient viability. Such a suspending medium, therefore, does not actually function to protect the cells, but rather only for diluting the freeze dried Bifidobacteria cells. In fact, the density of viable Bifidobacteria cells in the powdery products presently distributed in the market is very low.

There has not been known a powdery product containing dried Bifidobacteria cells which is capable of retaining a high density of viable cells during a prolonged storage period.

Therefore, it is an object of the present invention to provide a powdery composition containing dried viable Bifidobacteria cells in a high cell density which is capable of a higher cell survival rate during a long period of storage.

It is another object of the invention to provide a powdery composition containing dried viable Bifidobacteria cells which is capable of establishing Bifidobacterium flora in the intestinal tract when it is orally administered.

A further object of this invention is to provide a powdery composition comprising a powder containing viable Bifidobacteria cells and lactulose containing powder.

SUMMARY OF THE INVENTION

In accordance with this invention, these objects are accomplished by homogeneously admixing viable a powder containing Bifidobacteria cells with a powder containing lactulose.

In other words, this invention is predicated upon the discovery that admixing a specific quantity of a powder containing lactulose, having a major proportion of lactulose, as a suspending agent with a powder containing viable Bifidobacteria cells has a surprising effect in improving the cell survival rate.

The powder containing Bifidobacteria cells used in this invention comprises dried Bifidobacteria cells and a dispersing medium such as powdered skim milk, sodium glutamate, gelatine, lactose and the like, and includes at least $20 \times 10^{10}$ of viable Bifidobacteria cells in 1 gram thereof. Such a powder may be prepared by conventional methods.

The lactulose containing powder used in this invention includes at least 55% by weight of lactulose has a low moisture content. The remaining solid content may be residual lactose and galactose derived from the reaction mixture for lactulose preparation.

It is necessary that the final powdery composition product in accordance with this invention which is prepared by homogeneously admixing 40-70% by weight of the powder containing viable Bifidobacteria cells with 60-30% by weight of the lactulose containing powder contain at least $8 \times 10^{10}$ of viable Bifidobacteria cells in 1 gram of the final product, 28-57% by weight of lactulose and less than 2.5% by weight of moisture content in the final product.

The inventor confirmed that the powdery composition in accordance with this invention greatly improved cell survival rate of the Bifidobacteria cells after a relatively long period of storage and prevented decrease of the cell survival rate if the storage period was prolonged.

The microbial strain of Bifidobacteria cells used in this invention may be any known strain of species belonging to the genus Bifidobacterium, but it is preferable to use one or more selected from the group consisting of of Bifidobacterium adolescentis (ATCC 15703 and others), Bifidobacterium longum (ATCC 15707 and others), Bifidobacterium bifidum (ATCC 11146 and others) all of which can be normally found in the human intestinal tract at any age.

DETAILED DESCRIPTION OF THE PREFERRED EMBODIMENTS

In accordance with the inventor's discovery, the powdery composition of this invention includes viable Bifidobacteria cells and lactulose both in high concentration.

The powdery composition of this invention is obtainable by homogeneously admixing a powder containing viable Bifidobacteria cells and a powder containing lactulose.

The lactulose containing powder used for preparing the powdery composition of this invention is obtainable by any known method, for example, by drying lactulose syrup.

In Japanese Pat. No. 874,954 (Japanese Patent Publication No. 2984/1977), Nagasawa et al have disclosed that a lactulose syrup containing lactulose above 80% by weight in total solid content can be produced by admixing an aqueous solution of lactose with 2 to 10% by weight of an aqueous solution of sodium hydroxide containing from 0.27 to 0.54% of sodium hydroxide based on the weight of lactose, heating said mixed solution to a temperature of from 70° C. to 130° C. to isomerize the lactose and minimize formation of byproducts such as galactose and the other substances, and thereafter concentrating the reaction liquid to separate lactose from the reaction liquid (see U.S. Pat. No. 3,816,174, Belg. Pat. No. 783690, French Pat. No. 72/18213, Dutch Pat. No. 150513 and German Pat. No. 2224680).

A process for preparing a lactulose powder from lactulose syrup is disclosed in Japanese Pat. No. 778,564 (Japanese Patent Publication No. 49-44331 (See U.S. Pat. No. 3,716,408, Belg. Pat. No. 774451, French Pat. No. 71/38472, German Pat. No. 2148159, Dutch Pat. No. 147784 and U.K. Pat. No. 1318494). In accordance with the process, a lactulose powder containing more than 55% by weight of lactulose can be obtained by mixing an aqueous solution having a pH of less than 7.0 and containing more than 60% by weight of lactulose of its total solid content with an aqueous solution having dissolved, more than 0.3%, based on the weight of said lactulose, of KONNYAKU powder, and drying the resulting mixture by conventional hot air spray drying apparatus. (The KONNYAKU powder is derived from the corm of a perennial herb, "Amorphophalus konjac" belonging to the Araceae family and is mostly carbohydrate composed of mannan.)

In Japanese Patent Publication No. 52-21063, Nagasawa et al have also disclosed that a highly pure lactulose powder can be obtained by cooling lactulose syrup to between −20° C. and −45° C. in which range the syrup does not freeze, and subjecting it to freeze drying to produce a condensed syrup, and then heat-drying the condensed syrup until a dried porous mass is obtained, and finally pulverizing the porous mass into powder in a dehumidified atmosphere.

These methods are suitable for obtaining a powder containing more than 55% by weight of lactulose. Nowadays it has come to be possible to produce industrially highly pure lactulose powder up to 96% pure, and in this invention it is desirable to use highly pure lactulose containing powder as much as possible so as to insure a higher cell survival rate of the Bifidobacteria cells in the final product.

As will be described later, the moisture content of the final product is preferably less than 2.5% by weight, and for this reason the moisture content in the lactulose powder should be kept as low as possible, and preferably less than 0.7%.

The Bifidobacterium used in this invention may be any known strain of species belonging to the genus Bifidobacterium (see Bergey's Manual of Determinative Bacteriology, Eighth Edition, edited by R. E. Buchanan & N. E. Gibbones, pp. 669-676, 1974, The Willimas & Wilkins Co., Baltimore, U.S.A.;), but it is preferable to use one or more selected from the group consisting of of B. adolescentis (ATCC 15703 and others), B. longum (ATCC 15707 and others) and B. bifidum (ATCC 11146 and others) all of which can be normally found in the human intestinal tract at any age.

These strains are listed in the catalogue of Strains, Eleventh Edition (1974), The American Type Culture Collection, and are believed to be obtainable therefrom.

Any known fermentation methods and culture media for preparation of Bifidobacteria cells may be utilized, but the culture medium disclosed by Nagasawa et al in Japanese Early Opened Patent Application Publication No. 50-89587 is suitable, since microbial strains of genus Bifidobacterium may grow well in the culture medium and it is inexpensive. The culture medium contains corn steep liquor and fish liver as nitrogen sources; lactose, inorganic salts and cystine are added to form a desirable basic composition thereof; and extracts from rice bran or germs of various kinds of cereals are further added thereto.

The H-culture medium by Yuka Hara et al which contains meat extract, yeast extract, $KH_2PO_4$, $K_2HOP_4$, $CH_3COONa$, lactose and cystine and has a pH of 6.8 is also preferable, since it is easily prepared (see Journal of Japanese Society of Food and Nutrition, Vol. 18, No. 1 (1965), p. 10).

After proliferation, Bifidobacteria cells may be collected by centrifuging the culture medium. The collected cells are then suspended in sterilized isotonic sodium chloride solution of the same quantity as the culture medium, and are washed free from the culture medium and metabolites and the like which adhere to the surfaces of the cells, and are collected again by centrifuging the solution.

Normally about 6-10 grams of wet cells are obtained from 1 liter of the culture medium, and these wet cells contain $60-80 \times 10^9$ of Bifidobacteria cells per 1 gram thereof. The wet cells are then suspended in a sterilized aqueous solution, in the ratio of 60 grams of wet cells per 1 liter of the solution, containing 4% by weight of skim milk, 1% by weight of sodium glutamate, 0.4% by weight of gelatine, and 5% by weight of sucrose as suspending agent; thereafter the solution is freeze dried and pulverized into powder according to conventional methods. The thus obtained powder containing dried Bifidobacteria cells has a composition of about 74% by weight of the suspending agent, about 22% of dried cells, 4% or less of moisture content, and at least $20 \times 10^{10}$ of viable Bifidobacteria cells in 1 gram of the powder. The total percentages of suspending agent constituents equals 10.4% in the solution. Multiplying the 74% which corresponds to the weight of total suspending agent constituents in the dried composition by the ratio of the weight of each constituent to the total weight of suspending agent constituents in the solution, the percentages of suspending agents in the dried powder composition are 28% by weight of skim milk, 7% by weight of sodium glutamate, 3% by weight of gelatine, and 36% by weight of sucrose.

At least $20 \times 10^{10}$ of viable counts in 1 gram of the dried powder containing Bifidobacteria cells is necessary for obtaining the desirable high cell density of Bifidobacteria cells in the final product powdery composition. The moisture content in the dried powder containing Bifidobacteria cells is normally about 2.0%–4.0% by weight, but it is preferably as low as possible to increase cell survival rate in the composition.

The thus obtained dried powder containing Bifidobacteria cells and powder containing lactulose are mixed in a ratio of 40–70% and 60–30% by weight respectively by means of a V-type mixer under a low humidity atmosphere. The thus obtained powdery composition contains about 28–57% by weight of lactulose and 2.5% by weight or less of moisture content, and at least $8 \times 10^{10}$ of viable Bifidobacteria cells are contained in 1 gram of the powdery composition. It is necessary to keep the powdery composition in a cool and dark place, since the composition is very hygroscopic. The powdery composition may be packed in airtight container or placed in capsules and then packed in airtight containers for distribution. The proper dose of the powdery composition of this invention is 1–1.5 grams for infants, 1.5–3 grams for children and 3–6 grams for adults per day.

As previously mentioned, the cell survival rate of Bifidobacteria cells in the powdery composition of the present invention is highly increased by admixing lactulose and the powdery composition may contain viable Bifidobacteria cells in such a high cell density as about $10^3$ times of that of the conventional products which are diluted with a dispersing medium.

When the ratio of lactulose content to Bifidobacteria cells content is reduced in the powdery composition, the cell survival rate is decreased, and it has been noticed that lactulose content is preferably above 28% by weight of final product. It has been also found that when the ratio is increased too much, the cell survival rate is slightly decreased and moreover hygroscopicity of the powdery composition is increased by the lactulose powder which in turn results in a tendency of the powdery composition to agglomerate. As will be seen from the examples hereinafter described, it has been found that the lactulose content in the powdery composition is preferably less than 57% by weight. When the moisture content in the powdery composition is increased above 2.8% by weight, the cell survival rate rapidly decreases, and therefore it is practically important to keep the moisture content 2.5% by weight or less.

Now it will be understood that it is necessary, for preparing the powdery composition of this invention, to prepare a powder having a high cell density of Bifidobacteria cells and to prepare a powder containing a high concentration of lactulose.

It will come to be clear from the examples and the results of the comparative tests that the inventor of the present application has provided a powdery composition which contains viable Bifidobacteria cells in a high cell density, and shows excellent cell survival rate due to the admixing of lactulose, and is effective for establishment of a favorable state of intestinal flora as compared to the comparative samples wherein the lactulose containing powder is replaced with a conventional dispersing medium (such as starch and lactose).

EXAMPLE 1

Lactulose containing powder was prepared in the same manner as shown in example 1 of Japanese Patent No. 778564. That is, 3 Kg. of lactulose aqueous solution of pH 6.5 comprising 53.8% of lactulose, 8.2% of galactose, 6.3% of lactose, 31.1% of water and 0.6% of other materials (all by weight) was prepared. To 1.5 liters of water, 7.8 g (0.5% based on the lactulose content of the aqueous solution) of commercially available Konnyaku powder (milled powder, from Fukushima Prefecture, Japan) were added with stirring until uniformly swollen and filtered using a 100 mesh filter cloth to remove insolubles. The filtrate was added to said 3 Kg. of lactulose aqueous solution and then it was mixed well. This mixed solution was 140 cp in viscosity at 20° C. (measured by means of a B-type viscometer manufactured by Tokyo Keiki Co., Ltd. in accordance with the conventional method). The mixed solution was heated at 45° C. and then dried under the conditions of 170° C. hot air inlet temperature, 90° C. outlet temperature and 9,000 r.p.m. rotation velocity of atomizer by means of a spray dryer (manufactured by Anhydro Co.). One and three-quarters Kg. of white powder was obtained. The powder contained 78.2% by weight of lactulose content, 0.51% by weight of moisture content and was free flowing and easily soluble in water.

Powder containing Bifidobacteria cells was prepared by the method (hereinafter referred to method A) as described hereunder.

Culture medium was prepared in such a manner that 3.0% of fish liver, 2.0% of corn steep liquor, 2.0% of lactose, 0.1% of $KH_2PO_4$, 0.1% of $K_2HPO_4$, 0.5% of $CH_3COONa$ and 0.04% of 1-cystine (all by weight) were dissolved in 10 liters of water, and then the pH of the aqueous solution was adjusted to 6.8 by adding 1N aqueous solution of sodium hydroxide, and thereafter the solution was sterilized by means of an autoclave at 121° C. for 15 minutes and then cooled. Bulk starter culture of Bifidobacterium longum (ATCC 15707) was added to the culture medium to a concentration of 4% and mixed uniformly by stirring. Then fermentation was carried out anaerobically in a Jar Fermentor by gaseous carbon dioxide at 37° C. for 12 hours. During this fermentation, about 20% by weight of aqueous solution of $CaCO_3$ was added to the culture medium for adjusting its pH to about 7.

The culture medium was then cooled to 5° C. and centrifuged (10,000 r.p.m.) to collect the Bifidobacteria cells suspended therein by means of a refrigerated high speed continuous centrifuge, thereafter the thus collected cells were resuspended in 1000 ml of sterilized and cooled (5° C.) isotonic sodium chloride solution to wash away impurities, and then said resuspended solution was centrifuged (10,000 r.p.m.) to collect the washed bacterial cells.

Sixty g of the thus obtained wet Bifidobacteria cells were resuspended in 1 liter of sterilized aqueous solution of suspending agent comprising 40 g of sucrose, 15 g of mucin, 5 g of gelatine, 15 g of glutamic acid and 15 g of aspartic acid (aminosuccinic acid), and then freeze dried in accordance with conventional methods to obtain 96 g of Bifidobacteria cells powder containing 23.0% of the cells, 74.7% of suspending agent and 2.4% of moisture (all by weight). The viable count of the Bifidobacteria cells in 1 gram of the powder was $36 \times 10^{10}$.

Finally 90 g of said lactulose containing powder and 90 g of said powder containing Bifidobacteria cells were homogeneously mixed by means of a V-type mixer (by Tokuju Seisakusho Co., Ltd.) in a room kept at low humidity. Thereafter about 180 g of the powdery composition was placed in a red bottle and after being sealed airtight the bottle was stored at a cool, dark, and dry place. The thus obtained powder composition contained 39% by weight of lactulose and 1.46% by weight of moisture, and the viable count of the Bifidobacteria cells therein was $18 \times 10^{10}$/g.

EXAMPLE 2

In accordance with the method described in the example of the Japanese Patent Publication No. 52-21063, lactulose containing powder was prepared as follows:

Five hundred g of lactulose syrup composed of 56% of lactulose, 7.0% of galactose, 4.0% of lactose, 1.0% of other materials and 32% of water (all by weight) was poured to a depth of 5 mm in a pan in a shelved lyophilizer, and freeze drying was started at $-40°$ C., under vacuum of 1 mm Hg; and about 2 hours later the temperature in the lyophilizer was adjusted to $-30°$ C.; and then gradually raised to 80° C. over 4 hours, while the vacuum was gradually decreased to 30 mmHg. During this time, the syrup gradually bubbled up to a depth of 20 cm and became a uniform honeycomb like foamy mass. During a two hour period, the temperature was gradually adjusted to 35° C.; and then kept at that temperature for 16 hours and 340 g of a dried honeycomb like mass was obtained. During this time the vacuum was changed from $6 \times 10^{-2}$ mmHg to $2 \times 10^{-2}$ mmHg. The dried foamy mass was pulverized in a dehumidified chamber. The obtained powder was white and sufficiently free flowing and contained 80.8% by weight of lactulose and 0.5% by weight of moisture.

Powder containing Bifidobacteria cells was separately prepared by the same method as in example 1 except that Bifidobacterium adolescentis (ATCC 15705) was used (hereinafter referred to as method B). Ninety two grams of the powder containing Bifidobacteria cells was obtained. The viable count of the cells was $287 \times 10^9$/g, and it contained 3.0% by weight of moisture, 74.6% by weight of suspending agent and 22.4% by weight of the Bifidobacteria cells.

Forty grams of the previously obtained lactulose containing powder and 60 g of the obtained powder containing Bifidobacteria cells were homogeneously admixed in the same way mentioned in example 1, and about 100 g of powdery composition was obtained.

The viable count of the Bifidobacteria cells was $172 \times 10^9$/g, and it contained 32.3% by weight of lactulose and 2.02% by weight of moisture.

Test 1

A comparative test was conducted with respect to the relationship between cell survival rate and storage period.

The samples used in the test were Bifidobacteria cells containing powdery products A, B and C which were distributed by 3 companies A, B and C, a Bifidobacteria cells containing powder D as a comparative sample in which a conventional dispersing medium was used instead of the lactulose containing powder of the present invention and the powdery compositions obtained in examples 1 and 2 above.

The products A–C used in the test were the ones which had remaining effective terms of about 2.6 months calculated from the indications on their packages. Though it might possibly be that several months had elapsed from their manufacturing dates when they were purchased, in this test, they were treated on the supposition that they were manufactured on the day on which they were purchased.

50 g each of the products A–C were weighed in a dehumidified chamber in a vial bottle which was sealed to prevent access of moisture.

The comparative sample D was prepared by admixing 1 part by weight of Bifidobacteria cells containing powder obtained by the method A with 0.8 part by weight of starch and 0.2 part by weight of lactose as dispersing agent.

Fifty grams of the comparative sample D and the powdery compositions of examples 1 and 2 were also weighed respectively in the same bottles (capable of holding 100 ml), and then sealed to prevent access of moisture.

All of these 6 samples were stored for 6 months at 20° C., and further the samples of the examples 1 and 2 were stored for an additional 6 months.

The viable counts of the cells in the samples were determined by a method mentioned below at the times immediately after manufacturing (as to the samples A–C, immediately after purchasing), after 2 months storage, after 4 months storage and after 6 months storage for all samples, and after 12 months storage only for the samples of examples 1 and 2. Cell survival rates were calculated by using following equation.

$$\text{Cell Survival rate (\%)} = \frac{\text{Viable count after storage}}{\text{Viable count immediately after manufacturing}} \times 100$$

The method for determining viable counts is as follows:

Precisely weighed 1 gram samples of each were suspended in 9 ml of sterilized isotonic sodium chloride solution respectively. Each of the initial suspensions was diluted serially $10^2$ to $10^8$ times using sterilized isotonic sodium chloride solution. One ml of each diluted suspension was added to 9 ml of the semi-solid H-culture medium which was prepared by adding 0.5% of agar to the H-culture medium previously mentioned, and mixed homogeneously to make the finally diluted suspension. Each 5 ml of diluted suspension was poured into 4 Winberg tubes and incubated anaerobically at 37° C. for 48 hours in accordance with conventional methods. After incubation, Winberg tubes in which 30–300 colonies were formed were selected and the colonies were counted. The values of the arithmetic mean calculated from the numbers of colonies counted for each sample were considered to be the viable counts of the cells.

The results of this test are shown in Table 1.

TABLE 1

Viability of the cells in the samples

| samples | | storage immediately after manufacturing | after 2 months | after 4 months | after 6 months | after 12 months |
|---|---|---|---|---|---|---|
| A | viable count | $76 \times 10^5$ | $32 \times 10^5$ | $10 \times 10^5$ | $12 \times 10^5$ | |
|   | survival rate (%) | 100 | 42.1 | 13.2 | 15.8 | |
| B | viable count | $122 \times 10^5$ | $22 \times 10^5$ | $13 \times 10^5$ | $7 \times 10^5$ | |
|   | survival rate (%) | 100 | 18.0 | 10.7 | 5.7 | |
| C | viable count | $200 \times 10^4$ | $48 \times 10^4$ | $30 \times 10^4$ | $28 \times 10^4$ | |
|   | survival rate (%) | 100 | 24.0 | 15.0 | 14.0 | |
| D | viable count | $175 \times 10^9$ | $102 \times 10^9$ | $73 \times 10^9$ | $71 \times 10^9$ | |
|   | survival rate (%) | 100 | 58.3 | 41.7 | 40.6 | |
| Ex. 1 | viable count | $180 \times 10^9$ | $152 \times 10^9$ | $150 \times 10^9$ | $147 \times 10^9$ | $130 \times 10^9$ |
|   | survival rate (%) | 100 | 84.4 | 83.3 | 81.7 | 72.2 |
| Ex. 2 | viable count | $172 \times 10^9$ | $147 \times 10^9$ | $143 \times 10^9$ | $141 \times 10^9$ | $118 \times 10^9$ |
|   | survival rate (%) | 100 | 85.5 | 83.1 | 82.0 | 68.6 |

Note:
Viable count shows the viable count of Bifidobacteria cells in 1 gram of each sample.

As will be seen from Table 1, the cell survival rates after 6 months storage in the commercially available powders containing Bifidobacteria cells (samples A–C) are extremely low. The cell survival rate of the sample D is rather good as compared with that in the samples A–C, but it is not to be compared with those in the samples of examples 1 and 2 of this invention.

Test 2

A test was carried out for the influence of the ratio of lactulose containing powder to the bacterial cells (hereinafter referred to L/B ratio) on cell survival rate.

Lactulose powder containing 95.5% by weight of lactulose in solid content, 0.6% by weight of moisture was prepared in accordance with example 4 of Japanese Pat. No. 778564 in such a manner that 29.4 g, (0.5% based on the lactulose content) of commercially available konnyaku powder (milled powder, from Fukushima Prefecture, Japan) was added to 4.5 liters of water, while stirring, to cause uniform swelling and it was filtered using a 100 mesh filter cloth to remove insolubles. The filtrate was added to 3 Kg. of an aqueous lactulose solution of a pH of 6.4 and having a composition of 68.0% of lactulose, 1.2% of galactose, 0.1% of lactose, 30.0% of water and 0.7% of other materials (all by weight), obtained by epimerization of lactose, and, thereafter, oxidizing the aldose by product. This lactulose containing powder was admixed with powder containing Bifidobacteria cells prepared by the method A in different L/B ratios shown in Table 2 to obtain 9 samples of powdery compositions, and a test for viability of the cells was carried out by the same method as in Test 1. Meanwhile lactulose content and moisture content in the samples were determined by Sweeley's method (Journal of the American Chemical Society, Vol. 85 (1963); p. 1497) and by a conventional method respectively. The results of this test are shown in Table 2.

TABLE 2

Cell survival rates in the powdery compositions having different L/B ratios

| Sample Nos. | percentage of lactulose containing powder in the composition | percentage of B. cells containing powder in the composition | lactulose content in the samples (%) | moisture content in the samples (%) | viable counts of the B. cells in the sample immediately after manufacturing | viable counts of the B. cells in the sample after 6 months storage | cell survival rate after 6 months storage (%) |
|---|---|---|---|---|---|---|---|
| 1 | 70 | 30 | 66.9 | 1.14 | $108 \times 10^9$ | $77 \times 10^9$ | 71.3 |
| 2 | 65 | 35 | 62.1 | 1.22 | $124 \times 10^9$ | $96 \times 10^9$ | 77.4 |
| 3 | 62.8 | 37.2 | 60.0 | 1.27 | $133 \times 10^9$ | $106 \times 10^9$ | 79.7 |
| 4 | 60 | 40 | 57.3 | 1.30 | $144 \times 10^9$ | $119 \times 10^9$ | 82.6 |
| 5 | 50 | 50 | 47.8 | 1.50 | $180 \times 10^9$ | $147 \times 10^9$ | 81.7 |
| 6 | 40 | 60 | 38.2 | 1.69 | $215 \times 10^9$ | $173 \times 10^9$ | 80.5 |
| 7 | 30 | 70 | 28.7 | 1.86 | $252 \times 10^9$ | $202 \times 10^9$ | 80.2 |
| 8 | 25 | 75 | 23.9 | 1.95 | $273 \times 10^9$ | $162 \times 10^9$ | 59.3 |
| 9 | 20 | 80 | 19.1 | 2.03 | $287 \times 10^9$ | $121 \times 10^9$ | 42.2 |

Note:
Viable count shows the viable count of Bifidobacteria cells in 1 gram of each sample.

As will be apparent from Table 2, the samples 1–7 which contained above 28.7% of lactulose showed higher cell survival rates after 6 months storage. When the L/B ratio is increased to a certain level as in the samples 1–3, however, the powdery compositions tend to agglomerate due to the hygroscopicity of lactulose powder, though the survival rates are not much lowered.

Meanwhile, when the L/B ratio is decreased to a certain level as in the samples 8 and 9, survival rate is lowered and the containing powder as a suspending agent is decreased.

Accordingly, it has been found that the powdery composition of this invention preferably is prepared by admixing 40%–70% by weight of freeze dried Bifidobacteria cells containing powder with 60–30% by weight of lactulose containing powder, and the lactulose content in the resulting powdery composition preferably should be within a range of 28–57% by weight.

Test 3

A test was carried out for influence of moisture content in the powdery composition of this invention on the survival rate.

6 Samples of the powdery compositions were prepared by admixing the lactulose containing powder used in the Test 2 (95.5% by weight of lactulose in solid content, 0.6% by weight of moisture content) with powder containing Bifidobacteria cells prepared by method A but having different moisture contents.

These samples were subjected to a cell viability test by the same method as in Test 2. The results of this test are shown in Table 3.

TABLE 3

| Sample Nos. | moisture content of B. cells containing powder (%) | moisture content in the composition (%) | viable counts of the B. cells in the sample immediately after manufacturing | after 6 months storage | cell survival rates after 6 months storage |
|---|---|---|---|---|---|
| 1 | 5.62 | 3.13 | $122 \times 10^9$ | $9 \times 10^9$ | 7.4 |
| 2 | 5.08 | 2.83 | $153 \times 10^9$ | $68 \times 10^9$ | 44.4 |
| 3 | 4.42 | 2.51 | $182 \times 10^9$ | $145 \times 10^9$ | 79.7 |
| 4 | 3.75 | 2.16 | $182 \times 10^9$ | $149 \times 10^9$ | 81.9 |
| 5 | 2.40 | 1.49 | $170 \times 10^9$ | $137 \times 10^9$ | 80.6 |
| 6 | 2.06 | 1.33 | $177 \times 10^9$ | $148 \times 10^9$ | 83.6 |

Note:
Viable count shows the viable count of Bifidobacteria cells in 1 gram of each sample.

As will be clear from Table 3, the survival rate was considerably lowered when the powdery compositions contained above 2.51% by weight of moisture, and the survival rate was remarkably lowered when the moisture content was above 3% by weight.

It will be seen that the samples which had a moisture content less than 2.50% show more than 80% survival rate after 6 months storage. Accordingly it is essential that the moisture content in the powdery composition be less than 2.50% by weight.

tenth ml of the dilution was placed on an agar plate of H-culture medium containing added penicillin and agar in the ratio of 0.1 IU and 0.015 g per 1 ml of the culture medium respectively, and was spread evenly with an L-shaped glass rod. The colonies of the Bifidobacteria cells were counted after 72 hours anaerobic incubation at 37° C. by the steel wool method (Azuma et al, Japanese Journal of Bacteriology, Vol. 17 (1962), pp. 802-806, This method is a modification of Parker's method described in Australian Journal of Experimental Biology, Vol. 33 (1955), pp. 33-38).

The reason why penicillin containing H-culture medium was used was for restraining growth of bacteria other than genus Bifidobacterium on the agar plate. The results of this test are shown in Table 4.

TABLE 4

Effect of Bifidobacteria cells containing powder on establishment of intestinal flora

| subject Nos. | samples | viable count of B. cells/g in powdery composition | age of subject | sex of subject | after 3 days* | after 7 days* |
|---|---|---|---|---|---|---|
| 1 | Powdery composition of Example 1 of this invention | $180 \times 10^9$/g | 27 | ♀ | $38 \times 10^9$ | $28 \times 10^{10}$ |
| 2 | | | 45 | ♂ | $29 \times 10^8$ | $10 \times 10^{10}$ |
| 3 | Powdery composition of sample D in the Test 1 | $175 \times 10^9$/g | 23 | ♀ | $10 \times 10^5$ | $19 \times 10^9$ |
| 4 | | | 48 | ♀ | $< 10^5$ | $72 \times 10^8$ |
| 5 | Powdery composition of sample A in the Test 1 | $1 \times 10^4$/g** | 28 | ♀ | $< 10^5$ | $< 10^5$ |
| 6 | | | 23 | ♂ | $< 10^5$ | $71 \times 10^6$ |

*Viable count of Bifidobacteria cells/g.
**Viable count in the powdery composition of sample A is based on the instruction for dosage.

Test 4

In order to examine the efficacy of the powdery composition prepared by the invention for establishment of favorable intestinal flora, the following test was carried out using the powdery composition of example 1 of this invention, the powdery composition of sample D in Test 1 and the composition of sample A in Test 1.

Six subjects who were dosed with antibiotics for treating bowel complaints were taken for the test. Ages and sexes of the subjects are listed in Table 4. In all of their stools were observed less than $10^4$/g of stool of viable Bifidobacteria cells. As shown in Table 4, these subjects were separated into 3 groups, and 2 grams of each sample was administered to the subjects 3 times a day at fixed times for 7 consecutive days.

After 3 days and after 7 days from the beginning of treatment, stools of the 6 subjects were collected and 1 gram of each stool was suspended in 9 ml of sterilized isotonic sodium chloride solution. Each of these initial suspensions was serially diluted into $10^2$ to $10^8$ times using sterilized isotonic sodium chloride solution. One- As will be seen from Table 4, viable counts of the Bifidobacteria cells in the stools of the subjects (No. 1 and No. 2) who were treated with the powdery composition of this invention were $38 \times 10^9$/g, $29 \times 10^8$/g after only 3 days from the beginning of treatment, on the 7th day after treatment these increased to $28 \times 10^{10}$/g and $10 \times 10^{10}$/g respectively. The powdery composition of this invention, therefore, induced the predominance of Bifidobacteria cells in the intestinal flora of the subjects, since the total number of intestinal flora was around the level of $10^9$ to $10^{11}$ in 1 gram of stool.

Meanwhile, in the stools of the subjects (No. 5 and No. 6) who were treated with the powdery composition of sample A, viable counts of Bifidobacteria cells were not increased, and in one case (No. 5) among them viable count of Bifidobacteria cells was not found at the level of $10^5$ per 1 gram of stool after 7 days from the beginning of treatment. In the other case (No. 6), viable count of Bifidobacteria cells was observed at the level of $10^7$/g on the 7th day after the beginning of treatment, but such a low viable count cannot be considered to establish a favorable stage of intestinal flora.

In case of subjects (No. 3 and No. 4) who were treated with the powdery composition of sample D, only $19 \times 10^9$/g and $72 \times 10^8$/g viable counts of Bifidobacteria cells were observed even on the 7th day after the beginning of treatment. These values were rather close to those of the subjects (Cases 1 and 2) who were treated with the powdery composition of the present invention, but growing and indwelling of Bifidobacteria cells in the intestine was apparently delayed as compared to the above cases 1 and 2.

Now it will be understood that there are remarkable differences in the growing and indwelling of Bifidobacteria cells in the intestine between the subjects treated with sample D and the subjects treated with the powdery composition of the present invention, even though they are treated with almost the same level of Bifidobacteria cells, and therefore it is clear that the powdery composition of powder containing Bifidobacteria cells and lactulose containing powder in accordance with this invention is excellently efficient for the establishment of favorable intestinal flora.

As previously mentioned, the powdery composition of the present invention shows excellently high cell survival rate of Bifidobacteria cells during storage and may retain the high cell survival rate for a considerably long period, and moreover it is apparent that it may have the effect of establishing favorable intestinal flora.

In the light of foregoing descriptions, the powdery composition of the present invention is effective for establishing favorable intestinal flora by reducing saprogenic bacteria in the human intestine, and for treating constipation by increasing the viable count of Bifidobacteria cells upon administration, and also it is effective for treating portosystemic encephalopathy by reducing ammonium concentration in blood by restraining absorption of ammonia gas produced by digestion of protein in the intestinal tract.

Having now fully described the preferred embodiments of the present invention, it will be apparent to those skilled in the art that many modifications and changes can be made thereto without departing from the spirit and scope of the present invention.

I claim:

1. A powdery composition which contains 28–57 percent by weight of lactulose, less than 2.5 percent by weight of moisture and at least $8 \times 10^{10}$ of freeze dried viable cells of genus Bifidobacterium per gram of said composition.

2. The powdery composition of claim 1, wherein the microbial strain of said cells is selected from the group consisting of Bifidobacterium adolescentis, Bifidobacterium longum, Bifidobacterium bifidum and mixtures thereof.

3. The powdery composition of claim 1, wherein said composition is a mixture comprising:
   a. 40–70 percent by weight of a powdered mixture of said Bifidobacteria cells and a suspending agent therefor, containing at least $2 \times 10^{11}$ of said Bifidobacteria cells per gram, and
   b. 60–30 percent by weight of a powdered mixture containing at least 55 percent by weight of lactulose with the remainder consisting essentially of lactose and galactose.

4. The composition of claim 3, wherein said powdered mixture (a) consists of about 74 percent by weight of said suspending agent, about 22 percent by weight of freeze dried viable cells of genus Bifidobacterium and about 4 percent by weight of moisture.

5. The composition of claim 4 wherein said suspending agent consists of about 28 percent by weight of powdered skim milk, about 7 percent by weight of sodium glutamate, about 3 percent by weight of gelatin and about 36 percent by weight of sucrose.

* * * * *